United States Patent
Berg

[11] Patent Number: 5,720,857
[45] Date of Patent: Feb. 24, 1998

[54] SEPARATION OF 1,2,4-TRIMETHYLBENZENE FROM 1,2,3-TRIMETHYLBENZENE BY AZEOTROPIC DISTILLATION

[76] Inventor: Lloyd Berg, 13145 3rd Ave., Bozeman, Mont. 59715

[21] Appl. No.: 778,862

[22] Filed: Jan. 2, 1997

[51] Int. Cl.$^6$ .................................................. B01D 3/36

[52] U.S. Cl. .................. 203/57; 203/58; 203/60; 203/61; 203/62; 203/63; 203/64; 203/65; 203/67; 585/804; 585/865; 585/866; 585/867; 585/868

[58] Field of Search .......................... 203/57, 58, 60, 203/61, 62, 63, 64, 65, 67, 70; 585/800, 804, 807, 808, 865, 866, 867, 868

[56] References Cited

U.S. PATENT DOCUMENTS

| | | | |
|---|---|---|---|
| 3,987,120 | 10/1976 | Hosler | 203/35 |
| 4,021,311 | 5/1977 | Becker | 203/69 |
| 4,280,881 | 7/1981 | Montagna | 203/57 |
| 4,596,655 | 6/1986 | Van Eijl | 203/58 |
| 4,615,771 | 10/1986 | Zimmerman et al. | 203/63 |

FOREIGN PATENT DOCUMENTS

| | | | |
|---|---|---|---|
| 1543119 | 9/1969 | Germany | 203/57 |
| 0019722 | 3/1975 | Japan | 203/57 |

*Primary Examiner*—Virginia Manoharan

[57] ABSTRACT

1,2,4-Trimethylbenzene is difficult to sepparate from 1,2,3-trimethylbenzene because of the proximity of their boiling points. They are readily separated by azeotropic distillation. Effective agents are 1-propanol, methyl formate and 1-nitropropane.

1 Claim, No Drawings

SEPARATION OF 1,2,4-TRIMETHYLBENZENE FROM 1,2,3-TRIMETHYLBENZENE BY AZEOTROPIC DISTILLATION

FIELD OF THE INVENTION

This invention relates to a method of separating 1,2,4-trimethylbenzene from 1,2,3-trimethylbenzene using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirments.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 28 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of aromatic hydrocarbons in the cumene boiling range. Two of the close boiling found there are 1,2,4-trimethylbenzene and 1,2,3-trimethylbenzene which boil only seven degrees apart. A process to separate these two would enhance their value as pure compounds. The relative volatility between these two is only 1.3 which makes it difficult to separate them by conventional rectification Azeotropic distillation would be an attractive method of effecting the separation of these two if agents can be found that (1) will create a large apparent relative volatility among these two and (2) are easy to recover from the compound. Table 2 shows the relative volatility required to obtain 99% purity. With an agent giving a relative volatility of 1.6 only 27 actual plates are required.

TABLE 2

Theoretical and Actual Plates Required vs. Relative Volatility for Terpene Separation

| Relative Volatility | Theoretical Plates Required At Total Reflux, 99% Purity | Actual Plates Required 75% Efficiency |
|---|---|---|
| 1.4 | 28 | 38 |
| 1.3 | 22 | 30 |
| 1.6 | 20 | 27 |

OBJECTIVE OF THE INVENTION

The object of this invention is to provide a process or method of azeotropic distillation that will enhance the relative volatility of 1,2,4-trimethylbenzene from 1,2,3-trimethylbenzene in their separation in a rectification column. It is a further object of this invention to identify organic compounds which in addition to the above constraints, are stable, can be separated from the 1,2,4-trimethylbenzene and recyled to the column with little decomposition.

SUMMARY OF THE INVENTION

The objects of this invention are provided by a process for separating 1,2,4-trimethylbenzene from 1,2,3-trimethylbenzene which entails the use of certain organic compounds as the agent in azeotropic distillation.

DETAILED DESCRIPTION OF THE INVENTION

I have discovered that certain organic compounds will greatly enhance the relative volatility between 1,2,4-trimethylbenzene and 1,2,3-trimethylbenzene and permit separation by rectification when employed as the agent in azeotropic distillation. Table 3 lists the compounds that I have found to be effective in separating 1,2,4-trimethylbenzene from 1,2,3-trimethylbenzene by azeotropic distillation. They are ethanol, 1-propanol, 1-butanol, 2-methyl-1-butanol, 2-methyl-1-propanol, propyl acetate, 4-methyl-2-pentanone, 3-methyl-2-butanone, 2-ethoxyethanol, 1-methoxy-2-propanol, propylene glycol, tripropylene glycol, di-tert-butyl dicarbonate, methyl formate, ethyl lactate, methyl pivalate, n-butyl propionate, ethyl ether, 1,4-dioxane, propylene glycol propyl ether, 1-methoxy-2-propanol, mesityl oxide, butyronitrile, nitromethane, 1-nitropropane, 2-methoxyethanol and acetic acid.

TABLE 3

Effective Azeotropic Distillation Agents For Separating 1,2,4-Trimethylbenzene From 1,2,3-Trimethylbenzene

| Compounds | Relative Volatility |
|---|---|
| None | 1.3 |
| Ethanol | 1.4 |
| 1-Propanol | 1.6 |
| 1-Butanol | 1.5 |
| 2-Methyl-1-butanol | 1.4 |
| 2-Methyl-1-propanol | 1.5 |
| Propyl acetate | 1.4 |

TABLE 3-continued

Effective Azeotropic Distillation Agents For Separating 1,2,4-Trimethylbenzene From 1,2,3-Trimethylbenzene

| Compounds | Relative Volatility |
| --- | --- |
| 4-Methyl-2-pentanone | 1.45 |
| 3-Methyl-2-butanone | 1.4 |
| 2-Ethoxyethanol | 1.45 |
| Propylene glycol | 1.45 |
| Tripropylene glycol | 1.45 |
| Di-tert-Butyl dicarbonate | 1.4 |
| Methyl formate | 1.5 |
| Ethyl lactate | 1.5 |
| Methyl pivalate | 1.45 |
| n-Butyl propionate | 1.5 |
| Ethyl ether | 1.45 |
| 1,4-Dioxane | 1.4 |
| Propylene glycol propyl ether | 1.4 |
| 1-Methoxy-2-propanol | 1.6 |
| Mesityl oxide | 1.5 |
| Butyronitrile | 1.5 |
| Nitromethane | 1.4 |
| 1-Nitropropane | 1.5 |
| 2-Methoxyethanol | 1.5 |
| Acetic acid | 1.45 |

THE USEFULNESS OF THE INVENTION

The usefulness or utility of this invention can be demonstrated by referring to the data presented in Tables 1, 2 and 3. All of the successful agents show that 1,2,4-trimethylbenzene can be separated from 1,2,3-trimethylbenzene by means of azeotropic distillation in a rectification column and that the ease of separation as measured by relative volatility is considerable.

WORKING EXAMPLE

1. Fifty grams of a 1,2,4-trimethylbenzene - 1,2,3-trimethylbenzene mixture and 50 grams of 1-propanol were charged to a vapor-liquid equilibrium still and refluxed for five hours. Analyses indicated a vapor composition of 84.4% 1,2,4-trimethylbenzene, 15.6% 1,2,3-trimethylbenzene; a liquid composition of 77.2% 1,2,4-trimethylbenzene, 22.8% 1,2,3-trimethylbenzene. This is a relative volatility of 1.6.

I claim:

1. A method for recovering 1,2,4-trimethylbenzene from a mixture consisting of 1,2,4-trimethylbenzene and 1,2,3-trimethylbenzene which comprises distilling said mixture consisting of 1,2,4-trimethylbenzene and 1,2,3-trimethylbenzene in the presence of an azeotrope forming agent, recovering the 1,2,4-trimethylbenzene and the azeotrope forming agent as overhead product and obtaining the 1,2,3-trimethylbenzene as bottoms product, wherein said azeotrope forming agent consists of one material selected from the group consisting of ethanol, 1-propanol, 1-butanol, 2-methyl-1-butanol, 2-methyl-1-propanol, propyl acetate, 4-methyl-2-pentanone, 3-methyl-2-butanone, 2-methoxyethanol, 2-ethoxyethanol, 1-methoxy-2-propanol, propylene glycol, tripropylene glycol, di-tert.butyl dicarbonate, methyl formate, ethyl lactate, methyl pivalate, n-butyl propionate, ethyl ether, 1,4-dioxane, propylene glycol propyl ether, mesityl oxide, butyronitrile, nitromethane, 1-nitropropane and acetic acid.

* * * * *